United States Patent [19]

Rutner et al.

[11] 4,256,725

[45] Mar. 17, 1981

[54] PREPARATION OF SOLID SUBSTRATE CONTAINING RECEPTOR AND LABELED FORM OF LIGAND FOR ASSAYS

[75] Inventors: Herman Rutner, Hackensack, N.J.; Thomas F. Dodd, Bronx, N.Y.

[73] Assignee: Becton, Dickinson and Company, Paramus, N.J.

[21] Appl. No.: 879,902

[22] Filed: Feb. 21, 1978

[51] Int. Cl.² .................. G01N 33/16; B01J 1/22; A61K 39/00
[52] U.S. Cl. ................................. 424/1; 23/230 B; 422/68; 424/12; 424/16
[58] Field of Search ................... 424/1, 1.5, 8, 12; 23/230 B

[56] References Cited

U.S. PATENT DOCUMENTS

| | | | |
|---|---|---|---|
| 3,951,748 | 4/1976 | Devlin | 195/103.5 |
| 4,017,597 | 4/1977 | Reynolds | 424/1.5 |

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

A solid substrate is simultaneously contacted with a labeled form of a ligand to be assayed, a receptor for the ligand to be assayed and a solution of an ionic salt to produce a solid substrate which contains the labeled form of the ligand and the receptor. In a subsequent assay for the ligand, the solid substrate is contacted with a sample containing the ligand, whereby the labeled form of the ligand is available for equilibration with the receptor in competition with the ligand to be assayed.

20 Claims, No Drawings

PREPARATION OF SOLID SUBSTRATE CONTAINING RECEPTOR AND LABELED FORM OF LIGAND FOR ASSAYS

This invention relates to the assay of ligands, and more particularly, to a new and improved process for providing a solid substrate, which contains the labeled form of a ligand to be assayed, and a receptor for the ligand.

In U.S. Pat. No. 4,017,597 there is described an article suitable for use in the assay of ligands, in which a solid substrate contains a labeled form of ligand to be assayed and a receptor for the ligand. In accordance with the patent, such an article is prepared by the use of two separate sequential coating steps; initially coating the substrate with the receptor, followed by placing the labeled form of the ligand on the coated receptor.

The present invention is directed to an improved method of providing a solid substrate for use in an assay, in which a labeled form of ligand to be assayed, and a receptor for the ligand are deposited uniformly and concurrently on a solid substrate in a single step.

In accordance with the present invention, a solid substrate is simultaneously contacted with a labeled form of ligand to be assayed, a receptor for the ligand and an ionic solution, whereby the receptor and the labeled form of the ligand are placed on the substrate, with the labeled form of the ligand being available for equilibration with the receptor in competition with the ligand to be assayed when the substrate is contacted with a sample containing the ligand.

Applicant has found that by contacting the solid substrate with the three components, there can be provided a substrate which contains both the receptor and the labeled form of ligand, with the receptor being permanently placed on the substrate, and the labeled form of the ligand being available for equilibration with the receptor in competition with the ligand to be assayed, when the substrate is contacted with a sample containing the ligand. Although applicant does not intend to be limited by any theoretical reasoning, it is believed that labeled form of the ligand is placed either directly on the substrate and/or on the receptor which is on the solid substrate. As a result, as stated in the specification and claims, the terminology that the labeled form of the ligand is on the substrate and/or contained on the substrate covers both the state in which the labeled form of ligand is directly coated on the substrate and/or the state in which the labeled form of ligand is coated on the receptor which is on the substrate.

The ligand which is placed on the solid substrate, in labeled form, is any one of a wide variety of ligands for which an appropriate receptor can be found, such as (1) antigens, which when introduced into the blood stream of a vertebrate, result in the formation of antibodies; (2) haptens, which when bound to an antigenic carrier and introduced into the blood stream of a vertebrate, produce antibodies specific for the hapten, or (3) ligands which have naturally occurring receptors and also function as a hapten when bound to a protein.

As representative examples of ligands to which the present invention is applicable, there may be mentioned: polypeptides, nucleotides, nucleosides and proteins, such as ACTH, oxytocin, luteinizing hormone, insulin, proinsulin, chorionic gonadotropin, pituitary gonadotropin, growth hormone, renin, thyroxine binding globulin, bradykinin, angiotensin, follicle stimulating hormone, cyclic AMP, cholyl glycine, cyclic GMP, etc.; steroids, including: estrogens, gestrogens, androgens, adrenocortical hormones, bile acids, cardiotonic glycosides, aglycones as well as saponins. As specific examples, these may be mentioned: thyroxine, triiodothyronine, testosterone, androsterone, equilenin, estrone, estriol, progesterone, pregnenolone, 17-hydroxydioxycorticosterone (compound S), deoxycorticosterone, cortisone, corticosterone, cortisol, aldosterone, digoxin, digitoxin, etc.; vitamins, such as vitamin A, folic acid, the B vitamin group, vitamin C, the D vitamins, and vitamins E and K; and miscellaneous ligands, such as antigens for Viral Hepatitis A and B, Rubella, Herpes Simplex, α-fetoprotein, carcinoembryonic antigen, etc.

The above substances are only representative, and it is understood that such substances can be used as appropriate analogs and the term labeled form of the ligand includes such analogs.

The ligand is placed on the substrate in labeled form; i.e., the ligand applied to the solid substrate contains a "label", "tag" or "tracer", (such terms are interchangeably used in the art) which can be a radioisotope, an enzyme, a fluorescent material, etc. The use of such labels or tags and the procedures for preparing a ligand containing such label, tag or tracer are well known in the art and no further details in this respect are needed for a complete understanding of the invention. The preferred labeled ligand is radiolabeled, and as known in the art, such radioactive isotope is generally tritium or one of the radioisotopes of iodine.

The labeled form of ligand to be assayed and receptor therefor is placed on any one of a wide variety of solid materials, which are suitable as substrates for an assay. As known in the art, such materials include suitable polymers, such as polystyrene, polyethylene, polypropylene, polytetrafluoroethylene, polyamides, polyacrylamides, etc.; glass; bacterial cells; ion exchange resins; etc. Such solid carriers are known in the art and no further details in this respect are deemed necessary for a full understanding of the invention.

The solid substrate can be in particulate form, sheet form or in the form of a test tube, with a test tube being particularly preferred. The labeled form of the ligand and the receptor adhere to the solid substrate, by reversible and irreversible adsorption, respectively, to the solid phase; however, the scope of the invention is not limited thereby. The preferred solid phase is a plastic test tube, and in particular a tube formed of polystyrene or polypropylene.

The solution of an ionic salt employed in the coating technique of the present invention is a solution containing at least one salt, preferably an inorganic salt, which does not adversely affect the receptor and labeled ligand and provides a solution having an ionic strength of at least 0.5, and preferably at least 1.0. In general, the ionic strength of the solution does not exceed 10, and most generally does not exceed 5. The ionic strength of a solution is calculated or defined as follows:

Ionic Strength = $\frac{1}{2}\Sigma M_i Z_i^2$ wherein $M_i$ = molarity of ion; and $Z_i$ = charge of the ion Thus, the ionic strength is equal to one half the sum of the noted product for all ions present in the solution.

As representative examples of the inorganic salts which are employed to provide the ionic salt solution employed in the present invention, there may be mentioned: water soluble salts of ammonium and alkali metals; e.g., halides, sulfates, nitrates, phosphates, carbonates, bicarbonates, etc; water soluble salts of alkaline earth metals; e.g., halides nitrates, etc.; and the like. The salt and concentration are selected to provide the desired ionic strength. The solution may be conveniently provided as an aqueous solution.

Applicant has found that the use of an ionic salt solution provides for an effective placement of both the labeled form of the ligand and receptor on the solid substrate, with the labeled form of the ligand being available for equilibrium with the receptor in competition with a ligand to be assayed in a subsequent assay.

In accordance with the present invention, the solid substrate is simultaneously coated with the labeled form of the ligand, receptor and ionic salt solution, with such simultaneous coating being effected by concurrently but separately adding the three components, or by pre-incubating a mixture of the labeled form of ligand and receptor therefor, and concurrently but separately adding the pre-incubated solution and ionic salt solution. Thus, in accordance with the invention, the coating of the substrate is effected by having the substrate in contact with a mixture of the three components irrespective of the order of addition, with the conditions preferably being such that the three components are homogeneous in the contacting coating solution.

The contacting of the solid substrate with the three components is generally effected at a temperature in the order of from about 0° C. to about 37° C., and preferably from about 2° C. to about 9° C. The titer of the receptor in the solution is generally in the order of from about $1:10^3$ to about $1:10^6$, and the concentration of the labeled form of the ligand, in the solution, is generally in the order of from about $10^{-9}$ M to about $10^{-6}$ M or from $10^3$ to $10^5$ disintegrations per minute (DPM) per ml.

In the embodiment of the present invention wherein a mixture of the labeled form of the ligand and receptor therefor are pre-incubated, such pre-incubation is generally effected at a pH of from 6-8, although higher pH (8-10) or lower pH (3-6) can be employed. During the pre-incubation it is preferred to have a deaggregation agent present, such as glycine, to minimize aggregation of receptor proteins and association with labeled ligand. The use of pre-incubation offers the advantage that only two solutions need be handled during the actual coating and the further advantage that there is an equilibrated stable system which does not change during the coating step, thereby ensuring constant ratios of receptor and labeled ligand on the substrate.

The solid substrate, containing the labeled form of the ligand and receptor therefor can be employed for assays by procedures known in the art, except that only assay buffer and standard or unknown sample containing the ligand to be assayed need be added to the system. Thus, if the labeled form of the ligand is radiolabeled, the presence of ligand in a sample is determined by a radioimmunoassay, with the radiolabeled form of the ligand present on the solid substrate during the assay being available for equilibration with the coated receptor in competition with the ligand present in the sample, with the amount of the labeled form of the ligand which is bound to the receptor during the assay being dependent upon the quantity of unlabeled ligand to be assayed which is present in the sample. The amount of the radiolabeled form of the ligand present on the solid substrate and/or in the solution is determined by a suitable counter, and compared with a standard curve, as known in the art.

Similarly, if the labeled form of the ligand is enzyme labeled, the presence of ligand in the sample is determined by an enzyme determination procedure, as known in the art.

No details with respect to procedures for effecting the various assays are required for a complete understanding of the present invention in that such procedures are generally known in the art.

The present invention will be further described by reference to the following example; however, the scope of the invention is not to be limited thereby:

EXAMPLE 1

Two-reagent, sequential dispensing: Antiserum specific for conjugated bile acids, diluted 1:5,000 in 0.3% glycine and cholyl glycine histamine $^{125}$I tracer are incubated at 25° C. for 18 hours. Aliquots (0.1 ml) of incubated mixture containing antibody-tracer complex are dispensed into polystyrene or polypropylene test tubes followed by the sequential addition of 0.9 ml of coating solution containing 22% ammonium sulfate and 2.7% sodium chloride. After mixing, the mixture is incubated overnight at 4° C., and aspirated to remove excess unbound complex. The coated tubes are treated with 1.0 ml of a post coat solution (0.1% polyethylene glycol, M. W. 6000 (PEG) in 0.01 M, pH 7.4 potassium phosphate), aspirated and dried in vacuo prior to use in the assay.

EXAMPLE 2

Two-reagent, simultaneous dispensing: The test tubes are coated by dispensing the conjugated bile acid antibody-cholylglycine histamine $^{125}$I tracer complex after it has been pre-incubated 12 to 18 hours at 25° C. concurrently with the 22% ammonium sulfate $-2.7\%$ sodium chloride coating solution, via a glass mixing tee at a ratio of 1:9, respectively. Mixing occurs beyond the glass mixing tee and during discharge into the polystyrene or polypropylene tube to be coated. The tubes are incubated overnight at 4° C. and aspirated. The tubes are treated with 1.0 ml of post-coat solution (0.1% PEG 6000 in 0.01 M, pH 7.4 potassium phosphate) aspirated and dried in vacuo.

EXAMPLE 3

Three reagent, simultaneous dispensing: Antibody specific for conjugated bile acids (0.10 ml 1:5000 in 0.3% glycine), cholylglycyl-histamine $^{125}$I (0.10 ml, in 0.3% glycine containing 0.1% neomycin sulfate) and 22% ammonium sulfate 2.7% sodium chloride solution (0.80 ml) were dispensed simultaneously, via three separate dispensing pumps leading to a mixing manifold, into polystyrene or polypropylene test tubes. After incubation at 4° C. for 16 to 72 hours, the tubes were treated as in Example 1.

EXAMPLE 4

Three-reagent, sequential dispensing: The three reagents in Example 3 were dispensed sequentially as in Example 3 in the order antiserum, labeled ligand, salt solution. Further mixing after the last addition was effected by vortexing or sonification. Incubation and workup was done as in Example 1.

EXAMPLE 5

Example 1 is repeated, except antiserum specific for Digoxin was diluted 1:20,000 in 0.3 M glycine and incubated at 25° C. for 18 hours in the presence of digoxin $^{125}$I. The resultant digoxin antiserum-tracer complex was coated as in Example 1, but no post-coating step was used to prevent wash-off of the radio-ligand.

EXAMPLE 6

Example 3 was repeated, except digoxin anti-serum-tracer complex was coated in the presence of 0.5 M bicarbonate-carbonate buffer at pH 9.6. The balance of the coating process follows as in Example 1, but no post-coating step was used.

EXAMPLE 7

Example 1 was repeated, except used 0.5 M sodium iodide as coating solution.

EXAMPLE 8

Example 1 was repeated, except used 7.5 and 15% ammonium bicarbonate solution with and without the 2.7% sodium chloride at pH 9.0

Numerous modifications and variations of the present invention are possible in light of the above teachings and, therefore, within the scope of the appended claims, the invention may be practised otherwise than as particularly described.

We claim:

1. A process for preparing an article suitable for use in a solid phase assay, comprising:
   contacting a solid substrate with a mixture of the labeled form of a ligand to be assayed, a receptor for the ligand and a solution of an ionic salt having an ionic strength of at least 0.5, and no greater than 10.0 whereby the receptor and labeled form of the ligand are placed on the solid substrate, said labeled form of the ligand being reversibly placed on the solid substrate, whereby during an assay for the ligand, the labeled form of the ligand is available for equilibration with the receptor in competition with the ligand to be assayed.

2. The process of claim 1 wherein the labeled ligand is radiolabeled.

3. The process of claim 2 wherein the solid substrate is a plastic test tube.

4. The process of claim 1 wherein the solution of an ionic salt contains at least one member of the group consisting of water soluble salts of ammonium and alkali and alkaline earth metals.

5. The process of claim 4 wherein a mixture of the receptor and labeled form of the ligand are incubated prior to the contacting.

6. The process of claim 3 wherein the contacting is effected at a temperature of from 0° C. to 37° C.

7. The process of claim 6 wherein the ligand which is in labeled form is selected from the group consisting of antigens and haptens.

8. The process of claim 7 wherein a mixture of the receptor and labeled form of the ligand are incubated prior to the contacting.

9. The process of claim 7 wherein the solution of an ionic salt contains at least one member of the group consisting of water soluble salts of ammonium and alkali and alkaline earth metals.

10. An article suitable for use in a solid phase assay produced by the process of claim 1.

11. In a solid phase assay for a ligand in a sample wherein the sample is contacted with a solid substrate including a labeled form of the ligand and a receptor for the ligand, the improvement comprising:
    employing in the assay as said solid substrate an article produced by the process of claim 1.

12. The process of claim 5 wherein the preincubated mixture and the ionic solution are simultaneously applied to the solid substrate to provide said mixture.

13. The process of claim 5 wherein the preincubated mixture and the ionic solution are sequentially applied to the solid substrate to provide said mixture.

14. The process of claim 1 wherein the labeled form of the ligand, the receptor and the solution of an ionic salt are sequentially applied to the solid substrate to provide the mixture.

15. The process of claim 1 wherein the labeled form of the ligand, the receptor, and the solution of an ionic salt are simultaneously applied to the substrate to provide said mixture.

16. The process of claim 1 wherein the solution of an ionic salt has an ionic strength of at least 1.0 and no greater than 10.

17. The process of claim 4 wherein the solid substrate is a polymeric substrate.

18. The process of claim 17 wherein the polymer is selected from the group consisting of polystyrene and polypropylene.

19. The process of claim 18 wherein the receptor is a receptor for a conjugated bile acid and the labeled form of the ligand is a labeled form of a conjugated bile acid.

20. The process of claim 19 wherein the solution of an ionic salt contains ammonium sulfate and sodium chloride.

* * * * *